(12) United States Patent
Yonaha

(10) Patent No.: US 11,291,594 B2
(45) Date of Patent: Apr. 5, 2022

(54) ABSORBENT ARTICLE

(71) Applicant: DAIO PAPER CORPORATION, Ehime (JP)

(72) Inventor: Susumu Yonaha, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 447 days.

(21) Appl. No.: 16/348,606

(22) PCT Filed: Nov. 15, 2017

(86) PCT No.: PCT/JP2017/041102
§ 371 (c)(1),
(2) Date: May 9, 2019

(87) PCT Pub. No.: WO2018/097004
PCT Pub. Date: May 31, 2018

(65) Prior Publication Data
US 2020/0060893 A1   Feb. 27, 2020

(30) Foreign Application Priority Data

Nov. 25, 2016 (JP) ............................. JP2016-229539

(51) Int. Cl.
| A61F 13/511 | (2006.01) |
| A61F 13/533 | (2006.01) |
| A61F 13/47 | (2006.01) |

(52) U.S. Cl.
CPC ....... *A61F 13/51108* (2013.01); *A61F 13/511* (2013.01); *A61F 13/533* (2013.01); *A61F 2013/4708* (2013.01)

(58) Field of Classification Search
CPC .............. A61F 13/51108; A61F 13/511; A61F 13/533; A61F 2013/4708; A61F 13/51104
See application file for complete search history.

(56) References Cited

U.S. PATENT DOCUMENTS 9,381,122 B2   7/2016 Hashino et al.
9,492,331 B2   11/2016 Uematsu et al.
(Continued)

FOREIGN PATENT DOCUMENTS

JP   4757039       8/2011
JP   2014-068745   4/2014
(Continued)

OTHER PUBLICATIONS

International Search Report for PCT/JP2017/041102 dated Dec. 12, 2017.
(Continued)

*Primary Examiner* — Jessica R Arble
(74) *Attorney, Agent, or Firm* — IPUSA, PLLC

(57) ABSTRACT

An absorbent article includes compressed grooves formed in line symmetry with respect to a longitudinal centerline and including a pair of central compressed grooves, and a pair of front lateral side compressed grooves and a pair of rear lateral side compressed grooves formed on the front lateral side and the rear lateral side, respectively, of the central compressed grooves. The front and rear lateral side compressed grooves each includes a first arc-shaped compressed groove and a second arc-shaped compressed groove, positioned more distant from the centerline than the first arc-shaped compressed groove, which are disposed such that their respective inner circular arcs face each other. An extension line of the central compressed grooves passes between an end of the first compressed groove and an end of the second compressed groove, and does not pass between another end of the first compressed groove and another end of the second compressed groove.

6 Claims, 6 Drawing Sheets

(56) References Cited

U.S. PATENT DOCUMENTS

| | | |
|---|---|---|
| 10,195,090 B2 | 2/2019 | Kurihara |
| 2012/0088076 A1* | 4/2012 | Glakpe ............. A61F 13/51104 |
| | | 428/195.1 |
| 2013/0267926 A1* | 10/2013 | Uematsu ............. A61F 13/4758 |
| | | 604/385.101 |
| 2014/0296815 A1* | 10/2014 | Takken ............... A61F 13/5122 |
| | | 604/383 |
| 2017/0290718 A1 | 10/2017 | Takiyama et al. |

FOREIGN PATENT DOCUMENTS

| | | |
|---|---|---|
| JP | 2014-068958 | 4/2014 |
| JP | 5755856 | 7/2015 |
| JP | 2015-147035 | 8/2015 |
| JP | 2016-137102 | 8/2016 |

OTHER PUBLICATIONS

Extended European search report for European Patent Application No. 17874800.0 dated Oct. 14, 2019.

* cited by examiner

WIDTH
DIRECTION (a)

(b)

ABSORBENT ARTICLE

TECHNICAL FIELD

The present invention relates to absorbent articles.

BACKGROUND ART

Conventionally, as absorbent articles such as panty liners, sanitary napkins, and incontinence pads, those having an absorber provided between a liquid-permeable top sheet and a liquid-impermeable bottom sheet are known. Furthermore, in recent years, absorbent articles configured to more closely adhere to a body in order to prevent leakage of a body fluid are known.

For example, Patent Document 1 discloses an absorbent article having a skin contact surface in which compressed grooves are formed, where the compressed grooves include a pair of first central grooves disposed along a longitudinal direction in an excretory part contact region and a first annular groove positioned in at least one of a front region and a rear region and offset to one side in a width direction, the first annular groove being at a position overlapping the longitudinal centerline and including a curved portion and an inward-protruding bent point, the inward-protruding bent point being at a position not overlapping the longitudinal centerline.

Furthermore, Patent Document 2 discloses a sanitary napkin in which a left groove and a right groove that curve to bulge widthwise outward and a front groove and a rear groove that curve to bulge longitudinally outward in a plan view are provided on the skin contact surface side, where the grooves are separate from one another with the front ends of the left groove and the right groove being positioned longitudinally forward of and widthwise inside the rear end of the front groove and the rear ends of the left groove and the right groove being positioned longitudinally rearward of and widthwise inside the front end of the rear groove and with the left groove and the right groove being symmetrical in shape with respect to the longitudinal centerline and the widthwise centerline and the front groove and the rear groove being symmetrical in shape with respect to the longitudinal centerline.

PRIOR ART DOCUMENT

Patent Document

Patent Document 1: Japanese Patent No. 5755856
Patent Document 2: Japanese Patent No. 4757039

SUMMARY OF THE INVENTION

Problems to be Solved by the Invention

The absorbent article described in Patent Document 1 is configured in consideration of leakage of a body fluid from the perimeter of the absorbent article. The grooves, however, are connected or formed in succession. Therefore, in particular, a front side portion and a rear side portion are likely to become coarse, which may result in an uncomfortable fit.

According to the sanitary napkin described in Patent Document 2, a body fluid that diffuses forward and rearward along the left groove and the right groove may diffuse to the front lateral side and the rear lateral side, so that it may be impossible to prevent leakage to a satisfactory extent. Furthermore, Patent Document 2 describes an embodiment in which a pair of side grooves that curve to bulge widthwise inward are further provided along the side edges of the napkin. Such an embodiment, however, may cause more discomfort.

In view of the above-described points, the present invention has an object of providing an absorbent article that can satisfactorily prevent leakage of a body fluid from the front lateral side and the rear lateral side and provides a good fit.

Means for Solving the Problems

To solve the above-described problems, a first embodiment of the present invention is an absorbent article including an elongated body, the body including a liquid-permeable top sheet, a liquid-impermeable bottom sheet, and an absorber provided between the top sheet and the bottom sheet, wherein compressed grooves are formed in the body from the top sheet toward the bottom sheet, the compressed grooves include a pair of central compressed grooves formed substantially along a longitudinal direction of the body in line symmetry with respect to a centerline extending in the longitudinal direction of the body serving as an axis of symmetry, a pair of front lateral side compressed grooves formed in line symmetry with respect to the centerline serving as an axis of symmetry on a front lateral side of the central compressed grooves, and a pair of rear lateral side compressed grooves formed in line symmetry with respect to the centerline serving as an axis of symmetry on a rear lateral side of the central compressed grooves, each of the pair of the front lateral side compressed grooves and the pair of the rear lateral side compressed grooves includes a first compressed groove and a second compressed groove positioned more distant from the centerline than the first compressed groove, the first compressed groove and the second compressed groove have a circular arc shape, and are disposed such that inner circular arcs of both compressed grooves face each other, and an extension line of the central compressed grooves passes between an end of the first compressed groove and an end of the second compressed groove, and does not pass between another end of the first compressed groove and another end of the second compressed groove.

According to the above-described first embodiment, the pair of front lateral side compressed grooves and the pair of rear lateral side compressed grooves are provided on the front lateral side and the rear lateral side, respectively, of the central compressed grooves. Each of the pair of front lateral side compressed grooves and the pair of rear lateral side compressed grooves includes the first compressed groove and the second compressed groove. The first compressed groove and the second compressed groove have a circular arc shape, and are disposed such that the inner circular arcs of both compressed grooves face each other. An extension line of the central compressed grooves passes between an end of the first compressed groove and an end of the second compressed groove, and does not pass between another end of the first compressed groove and another end of the second compressed groove. This makes it possible to easily draw a body fluid that has diffused forward and rearward along the central compressed grooves into the front lateral side compressed grooves and the rear lateral side compressed grooves. Specifically, it is possible to draw in a body fluid between the first compressed groove and the second compressed groove and to guide the body fluid such that the body fluid meanders along a path formed between the first compressed groove and the second compressed groove. As a result, it is possible to control diffusion of the body fluid to the front lateral side and the rear lateral side and to satisfactorily prevent leakage to the front lateral side and the rear lateral side.

Furthermore, according to this embodiment, the extension line of the central compressed grooves passes between the first compressed groove and the second compressed groove. The central compressed grooves and the front lateral side compressed grooves are not provided in succession, and the central compressed grooves and the rear lateral side compressed grooves are not provided in succession. Therefore, it is possible to reduce coarseness due to the compressed grooves. Furthermore, it also contributes to reduction in coarseness that each of the front lateral side compressed grooves and the rear lateral side compressed grooves includes the first compressed groove and the second compressed groove that are two separate compressed grooves having a circular arc shape.

According to a second embodiment of the present invention, a line segment connecting both ends of the first compressed groove and a line segment connecting both ends of the second compressed groove form an angle of 30° to 60° with the centerline.

According to the above-described second embodiment, the first compressed groove and the second compressed groove are inclined to a predetermined direction. Therefore, in particular, the action of controlling sideward diffusion of a body fluid is further exerted, so that it is possible to further improve the effect of preventing leakage of a body fluid to the front lateral side and the rear lateral side.

According to a third embodiment of the present invention, in a direction in which a line segment connecting both ends of the first compressed groove extends, the end of the second compressed groove closer to the central compressed grooves is offset to one side in the direction relative to the end of the first compressed groove closer to the central compressed grooves, and the end of the second compressed groove more distant from the central compressed grooves is offset to the one side in the direction relative to the end of the first compressed groove more distant from the central compressed grooves.

According to the above-described third embodiment, the first compressed groove and the second compressed groove are offset in a predetermined direction. Therefore, the action of drawing in a body fluid running through the central compressed grooves between the first compressed groove and the second compressed groove and the action of guiding the body fluid by causing the body fluid to meander are further improved, so that it is possible to satisfactorily prevent leakage from the side in particular even when the body fluid is suddenly discharged.

According to a fourth embodiment of the present invention, in the direction in which the line segment connecting both ends of the first compressed groove extends, the distance between the midpoint of the line segment connecting both ends of the first compressed groove and the end of the second compressed groove closer to the central compressed grooves is 0 to 0.15 times the length of the line segment connecting both ends of the first compressed groove.

According to the above-described fourth embodiment, by causing the offset of the first compressed groove and the second compressed groove to fall within a predetermined range, it is possible to further improve the action of drawing in a body fluid between the first compressed groove and the second compressed groove. Furthermore, it is possible to prevent hardening of the absorber, so that it is possible to further improve a fit.

According to a fifth embodiment of the present invention, the distance between the line segment connecting both ends of the first compressed groove and the line segment connecting both ends of the second compressed groove is 0 to 0.2 times the length of the line segment connecting both ends of the first compressed groove.

According to the above-described fifth embodiment, the first compressed groove and the second compressed groove face each other in a predetermined arrangement. Therefore, the effect of drawing in a body fluid between the first compressed groove and the second compressed groove is further improved.

According to a sixth embodiment of the present invention, the first compressed groove and the second compressed groove has a shape of a circular arc having an angle of 135° to 180°.

According to the above-described sixth embodiment, because the circular arc shape of the first compressed groove and the second compressed groove has a predetermined angle of 180° or less, it is possible to prevent the absorber from becoming hard and coarse and to improve a fit while maintaining the action of drawing in a body fluid between the first compressed groove and the second compressed groove.

Effects of the Invention

According to an embodiment of the present invention, an absorbent article that can satisfactorily prevent leakage of a body fluid from the front lateral side and the rear lateral side and provides a good fit is provided.

EMBODIMENT OF THE INVENTION

An embodiment of the present invention is described below with reference to the drawings.

[Basic Structure of Absorbent Article]

Figure 1:
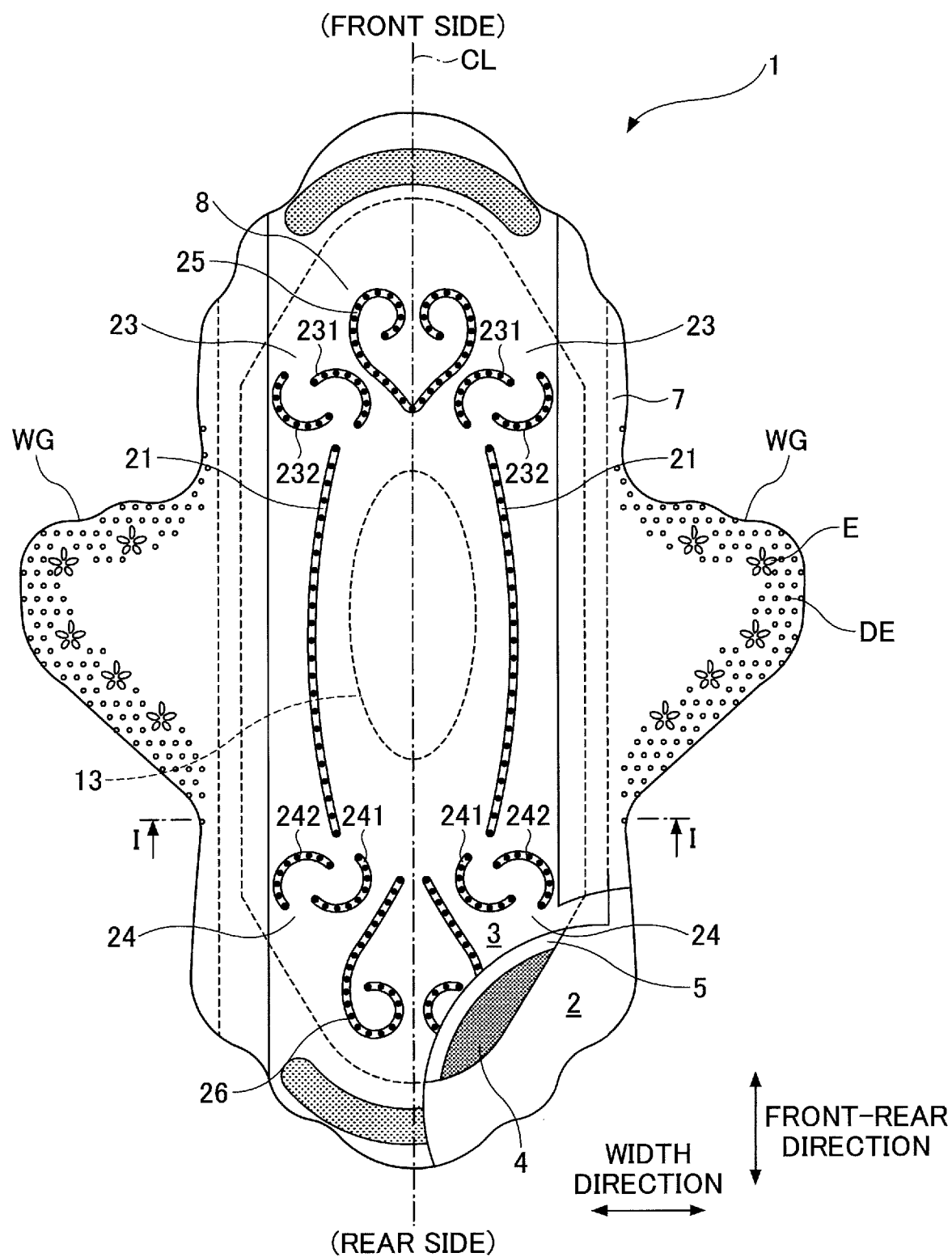
FIG. 1 is a partial cutaway view of an absorbent article according to an embodiment of the present invention.
Figure 2:
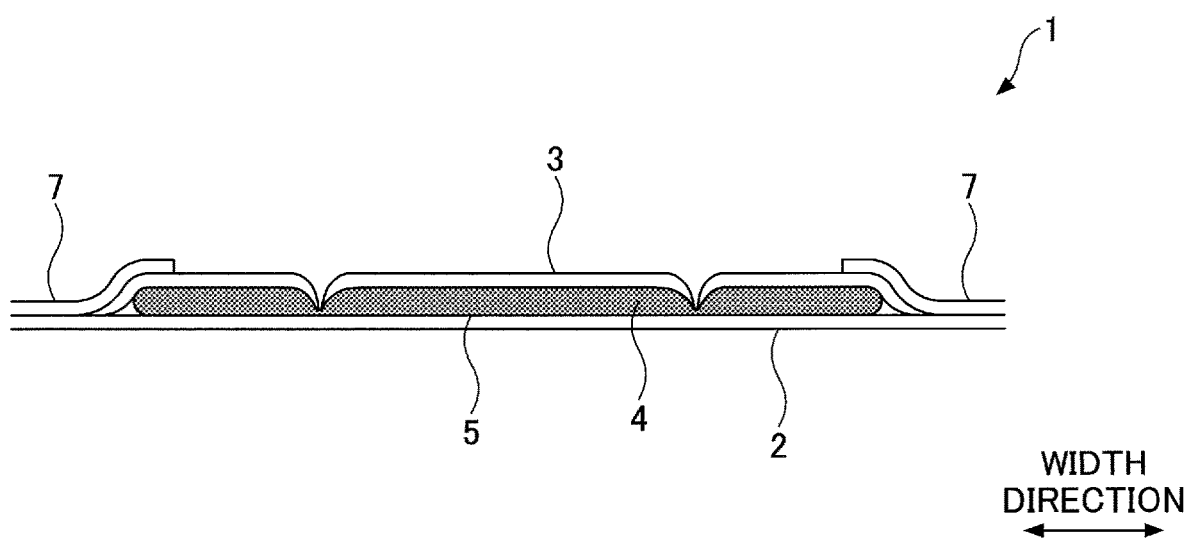
FIG. 2 is a cross-sectional view of the absorbent article according to the embodiment of the present invention, taken along the line I-I.

As illustrated in FIGS. 1 and 2, an absorbent article 1 includes a body (absorbent article body) 8 that includes a liquid-impermeable bottom sheet 2, a liquid-permeable top sheet 3, and an absorber 4 provided between these sheets 2 and 3. To maintain the shape of the absorber 4, the absorber 4 may be enveloped in an enveloping sheet 5 made of crepe paper, nonwoven fabric or the like.

As illustrated in FIG. 1, as a whole, the body 8 is elongated to have a predetermined length in the front-rear direction, and has a substantially fixed width in a direction perpendicular to the front-rear direction. The absorbent article 1 has a substantially line-symmetric shape with respect to a centerline CL extending in the front-rear direction.

At the front and the rear end edge of the absorber 4, the outer edge of the bottom sheet 2 and the outer edge of the top sheet 3 are joined by an adhesive such as a hot glue or bonding means such as heat sealing or ultrasonic sealing. Furthermore, side nonwoven fabrics 7 are provided one on each side of the top sheet along the front-rear direction (longitudinal direction). The side nonwoven fabrics 7 partially protrude sideways relative to the body 8, and are stacked on and joined by an adhesive such as a hot glue or bonding means such as heat sealing or ultrasonic sealing to the bottom sheet 2 that also protrudes sideways, thereby forming wings WG on both sides of the body 8.

A sheet material that is at least impervious to water, such as a sheet of an olefin resin such as polyethylene or polypropylene, may be used as the bottom sheet 2. A laminate nonwoven fabric that is a laminate of a polyethylene sheet or the like and a nonwoven fabric, and a laminated sheet of nonwoven fabrics that substantially ensures liquid impermeability by interposing a waterproof film may be used. Furthermore, in light of prevention of stuffiness, it is further desired to use one with moisture permeability. As such a water-impervious and moisture-permeable sheet material, a microporous sheet obtained by forming a sheet by dissolving and mixing inorganic filler in an olefin resin such as polyethylene or polypropylene, and thereafter stretching the sheet in one axial or two axial directions, may be used.

The top sheet 3 is a liquid-permeable sheet that allows quick passage of a body fluid such as menstrual blood, vaginal discharge, or urine. As the top sheet 3, a porous or nonporous nonwoven fabric or a porous plastic sheet is preferably used. Examples of fiber materials of the nonwoven fabric include synthetic fibers of olefin such as polyethylene or polypropylene, polyester, or polyamide; regenerated fibers such as rayon and cuprammonium rayon; mixed fibers of these; and natural fibers such as cotton, which may be used alone or in any combination. Furthermore, methods of processing the nonwoven fabric include spunlacing, spunbonding, thermal bonding, melt blowing, and needle punching. Of these processing methods, spunlacing is preferable in being capable of manufacturing a nonwoven fabric with good flexibility, spunbonding is preferable in being capable of manufacturing a nonwoven fabric with good drapability, and thermal bonding is preferable in being capable of manufacturing a lofty, soft nonwoven fabric. Furthermore, composite fibers such as sheath-core fibers having a high-melting-point fiber as a core and a low-melting-point fiber as a sheath, side-by-side fibers, and split fibers may be used.

The absorber 4 interposed between the bottom sheet 2 and the top sheet 3, whose material is not limited as long as it can absorb and hold a body fluid, preferably includes cotton pulp and a water absorptive polymer. Usable water absorptive polymers include superabsorbent polymers (SAPs), superabsorbent fibers (SAFs), and their mixtures. Examples of pulp include those made of cellulose fibers, such as chemical pulp and dissolving pulp obtained from wood, and those made of artificial cellulose fibers such as rayon and acetate. While hardwood materials and softwood materials are used as raw materials of chemical pulp, softwood materials are suitably used because of long fiber length.

Synthetic fibers may be mixed into the absorber 4. Usable synthetic fibers include polyolefins such as polyethylene and polypropylene, polyesters such as polyethylene terephthalate and polybutylene terephthalate, polyamides such as nylon, and their copolymers, of which two may be used in mixture. Furthermore, composite fibers such as sheath-core fibers having a high-melting-point fiber as a core and a low-melting-point fiber as a sheath, side-by-side fibers, and split fibers may also be used. Hydrophobic fibers subjected to surface treatment with a hydrophilizing agent to be provided with affinity for body fluids may also be used.

The thickness of the absorber 4 may range from 0.5 to 25 mm, preferably from 1.5 to 6.5 mm. The absorber 4 does not have to be uniform in thickness in its entirety, and may include a bulging portion corresponding to where a body fluid is discharged. The absorber 4 is preferably manufactured by fiber stacking or air laying.

As the side nonwoven fabrics 7, a water-repellant nonwoven fabric or a hydrophilized nonwoven fabric may be used. For example, in the case of improving an anti-permeation effect against menstrual blood, vaginal discharge or the like, or the feel of texture, it is preferable to use a water-repellant nonwoven fabric coated with a silicon, paraffin, or alkyl chromic chloride water repellent. In the case of improving the capability of absorbing menstrual blood or the like, it is preferable to use a hydrophilized nonwoven fabric as the material of a nonwoven fabric. A preferable type of nonwoven fabric is an air through nonwoven fabric that is less likely to develop folds, wrinkle-resistant, and soft.

As illustrated in FIG. 1, in order to join the side nonwoven fabrics 7 and the bottom sheet 2 and increase stiffness, an embossed portion provided with dot embossments DE and embossments E having a predetermined shape may be provided in a predetermined area on the outer edges of the wings WG.

The overall length of the absorbent article 1 may be 130 to 450 mm, may be 140 to 360 mm, or may be 170 to 270 mm.

[Compressed Grooves]

As illustrated in FIG. 1, multiple compressed grooves are provided in the absorbent article 1 of this embodiment. These compressed grooves (also referred to as fit embossments) are provided in the top sheet 3 toward the bottom sheet 2 to make it easier for the absorbent article 1 to so deform as to fit the shape of the body of a user, in order to improve a fit to the body.

The compressed grooves are formed in line symmetry with respect to the centerline CL extending in a longitudinal direction serving as an axis of symmetry. The compressed grooves include a pair of substantially rectilinear central compressed grooves 21, 21 extending along the longitudinal direction, a pair of front lateral side compressed grooves 23, 23 formed on the front lateral side (diagonally forward of) the central compressed grooves 21, 21, and a pair of rear lateral side compressed grooves 24, 24 famed on the rear lateral side (diagonally rearward of) the central compressed grooves. The compressed grooves may further include a front compressed groove 25 substantially having a heart shape as viewed in FIG. 1, extending further forward from between the front lateral side compressed grooves 23, 23, and a rear compressed groove 26 substantially having an inverted heart shape as viewed in FIG. 1, extending further rearward from between the rear lateral side compressed grooves 24, 24.

The compressed grooves, which are equal in width according to the illustrated embodiment, may be different in width from one another. Furthermore, a single compressed groove may be uniform or vary in width. Furthermore, the compressed grooves according to the illustrated embodiment include a low compressed portion and a high compressed portion famed deeper than the low compressed portion. In the drawings, of the compressed grooves, high compressed grooves are shown in black and low compressed grooves are shown in white.

The central compressed grooves 21, 21 are disposed substantially along the longitudinal direction in such a manner as to flank a region corresponding to a body fluid discharge portion when attached (hereinafter also referred to as body fluid discharge portion corresponding region) 13. The central compressed grooves 21, 21 can serve to prevent the body 8 including the absorber 4 from twisting and to prevent sideward leakage of a discharged body fluid by controlling sideward diffusion (seepage) of the body fluid. According to the configuration of FIG. 1, the central compressed grooves 21, 21 are so shaped as to slightly curve toward the longitudinal centerline CL (inward), namely, so shaped as to be closer to the centerline CL toward both ends. Alternatively, the central compressed grooves 21, 21 may extend straight or may be so shaped as to curve outward, namely, so shaped as to be more distant from the centerline CL toward both ends.

The pair of front lateral side compressed grooves 23, 23 are disposed laterally in at least two locations as viewed in FIG. 1 where the absorber 4 starts to narrow toward the front. Furthermore, the pair of rear lateral side compressed grooves 24, 24 may be disposed laterally in at least two locations as viewed in FIG. 1 where the absorber 4 starts to narrow toward the rear.

Furthermore, in the width direction, the front lateral side compressed grooves 23, 23 and the rear lateral side compressed grooves 24, 24 lie beyond the outermost positions of the pair of central compressed grooves 21, 21 (the positions most distant from the centerline CL). That is, as illustrated in FIG. 1, the central compressed grooves 21, 21 are positioned inside (at positions closer to the centerline CL than) the outermost positions in the width direction to which the front lateral side compressed grooves 23, 23 and the rear lateral side compressed grooves 24, 24 extend. Therefore, it is possible to particularly reduce coarseness around the legs, which are susceptible to discomfort, and it is possible to improve a fit during walking and exercise.

Each of the front lateral side compressed grooves 23, 23 includes a first compressed groove 231 and a second compressed groove 232 positioned more distant from the longitudinal centerline CL than the first compressed groove 231. Furthermore, each of the rear lateral side compressed grooves 24 includes a first compressed groove 241 and a second compressed groove 242 positioned more distant from the longitudinal centerline CL than the first compressed groove 241. That is, the front lateral side compressed grooves 23, 23 and the rear lateral side compressed grooves 24, 24 may include at least eight compressed grooves in total.

Each of the first compressed groove 231 and the second compressed groove 232 included in the front lateral side compressed groove 23 has a circular arc shape. The first compressed groove 231 and the second compressed groove 232 are disposed such that the inner circular arcs of the compressed grooves 231 and 232 face each other, namely, such that the first compressed groove 231 and the second compressed groove 232 become closer to each other toward both ends. Likewise, each of the first compressed groove 241 and the second compressed groove 242 included in the rear lateral side compressed groove 24 has a circular arc shape. The first compressed groove 241 and the second compressed groove 242 are disposed such that the inner circular arcs of the compressed grooves 241 and 242 face each other.

The first compressed groove and the second compressed groove included in the front lateral side compressed groove 23 and the rear lateral side compressed groove 24 may be equal in shape to or different in shape from each other. Furthermore, the first compressed groove and the second compressed groove may be equal in size to or different in size from each other.

The shape and arrangement of the front lateral side compressed grooves 23, 23 and the rear lateral side compressed grooves 24, 24 are described in more detail below. Each of FIGS. 3 through 5 is a partially enlarged schematic diagram of the absorbent article 1 of this embodiment, illustrating an arrangement of one of the front lateral side compressed grooves 23.

Figure 3:
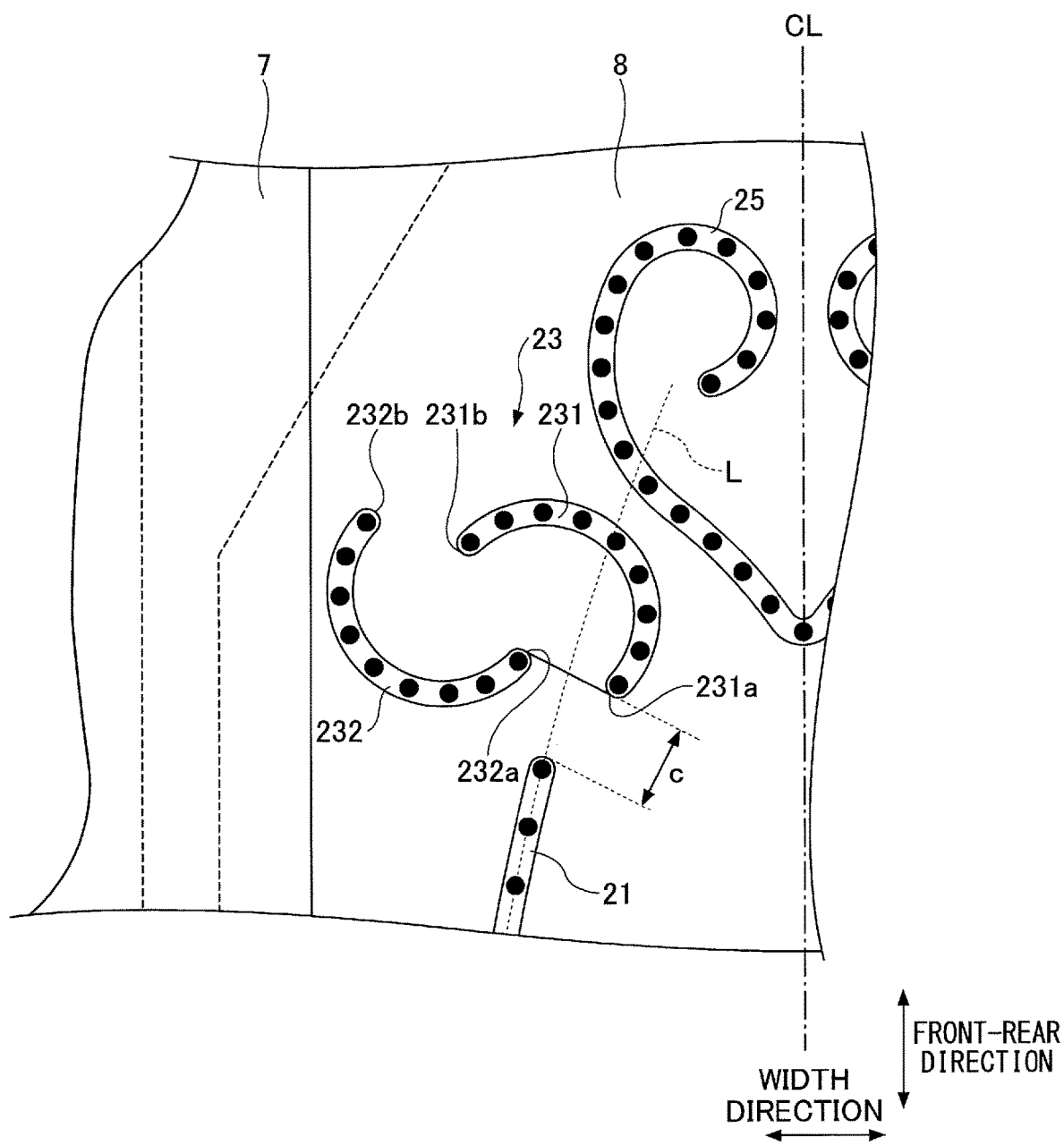
FIG. 3 is a diagram illustrating compressed grooves of the absorbent article according to the embodiment.
Figure 4:
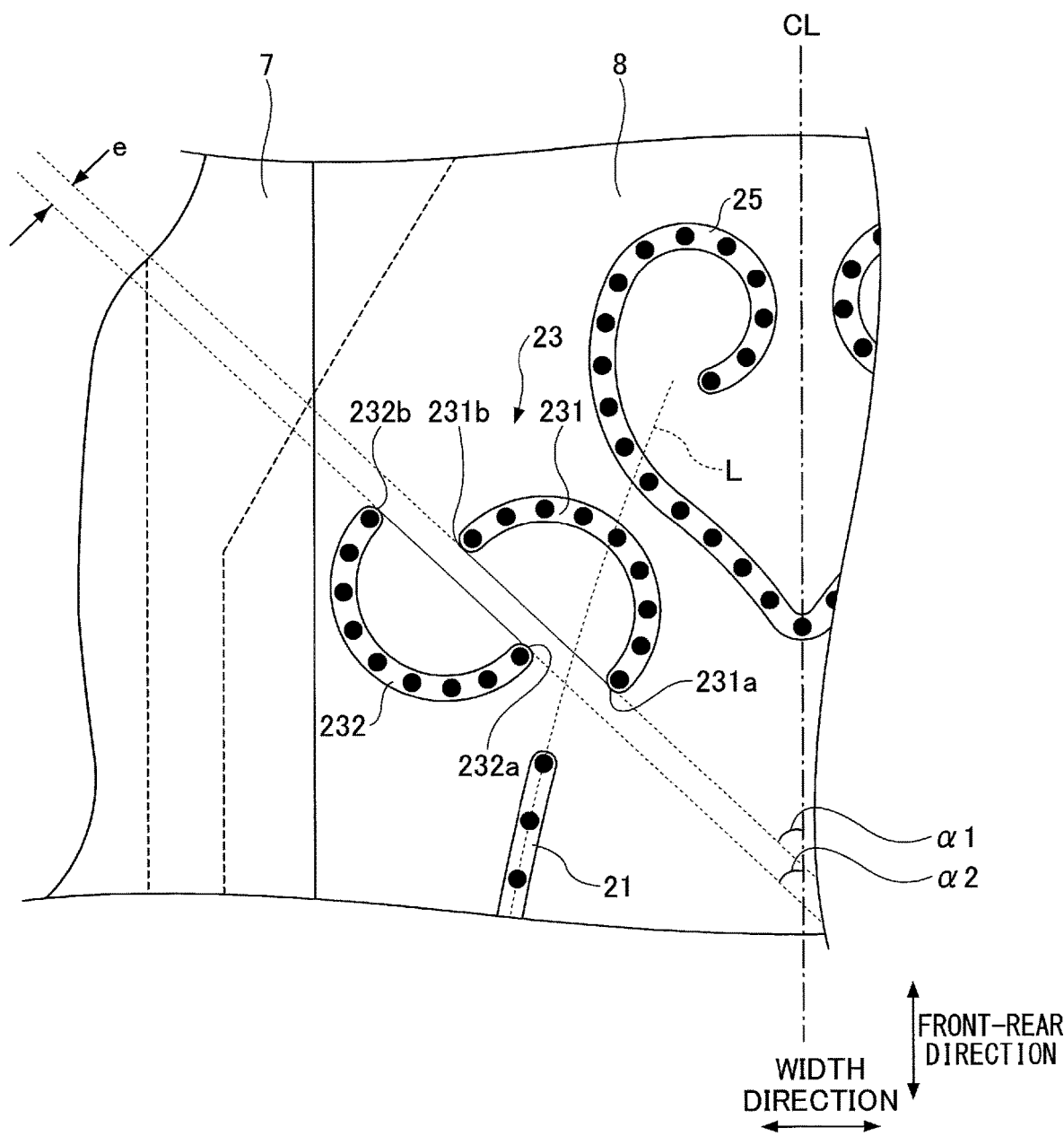
FIG. 4 is a diagram illustrating the compressed grooves of the absorbent article according to the embodiment.
Figure 5:
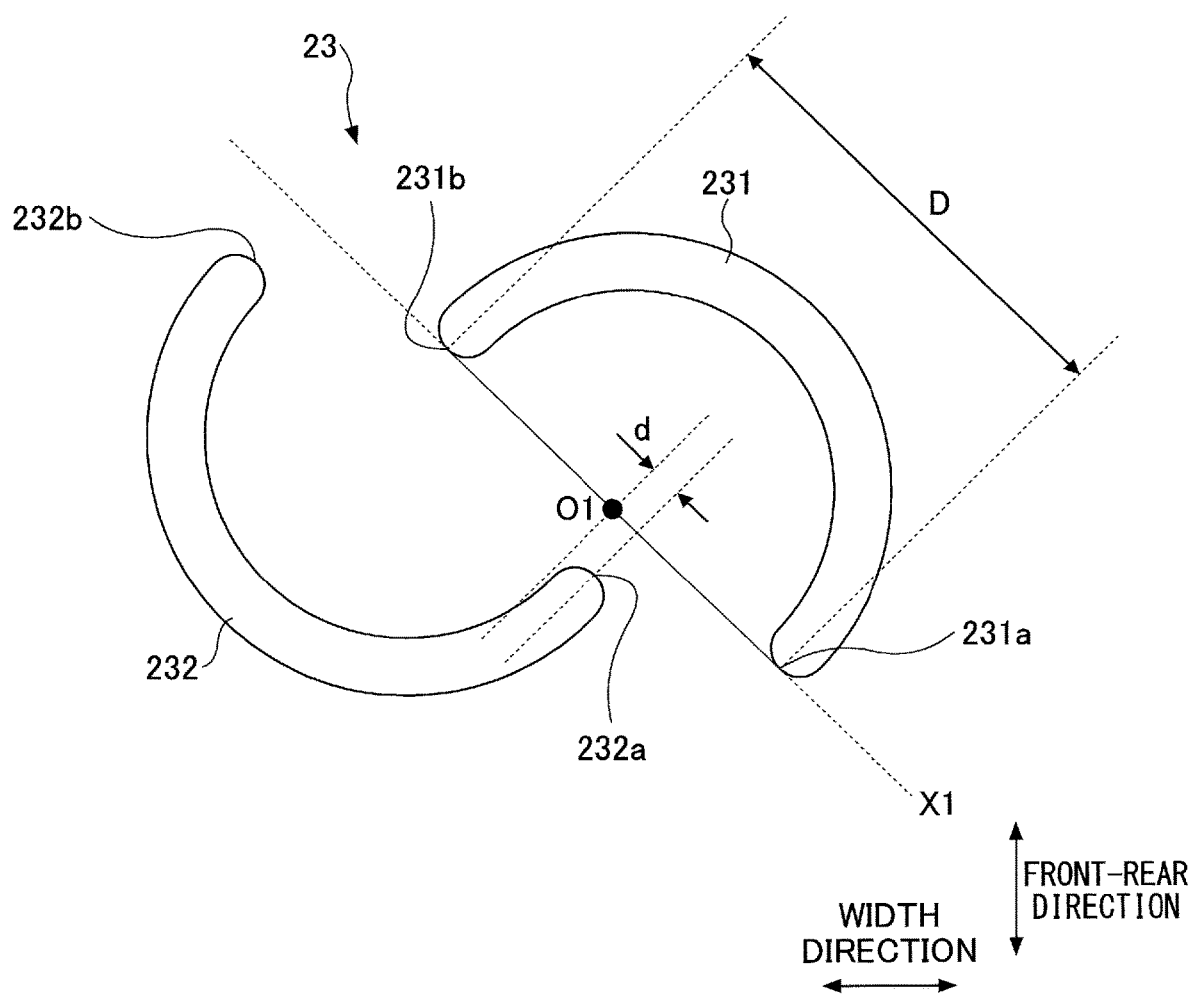
FIG. 5 is a diagram illustrating the compressed grooves of the absorbent article according to the embodiment.

While one of the front lateral side compressed grooves 23 is illustrated as a typical example in FIGS. 3 through 5, the front lateral side compressed grooves 23, 23 and the rear lateral side compressed grooves 24, 24 provided in at least four locations may have the same basic configuration. The pair of front lateral side compressed grooves 23, 23 and the pair of rear lateral side compressed grooves 24, 24 may differ from each other in one or more of the shape, size, and arrangement (including the positional relationship of the first compressed groove and the second compressed groove) of compressed grooves.

The front lateral side compressed groove 23 is positioned in a predetermined positional relationship with the central compressed groove 21. That is, as illustrated in FIG. 3, an extension line L of the central compressed groove 21 passes between one end 231a of the first compressed groove 231 and one end 232a of the second compressed groove 232 and does not pass between another end 231b of the first compressed groove 231 and another end 232b of the second compressed groove 232.

Specifically, the extension line L of the central compressed groove 21 passes between the end 231a of the first compressed groove 231 closer to the central compressed groove 21 and the end 232a of the second compressed groove 232 closer to the central compressed groove 21, and does not pass between the end 231b of the first compressed groove 231 more distant from the central compressed groove 21 and the end 232b of the second compressed groove 232 more distant from the central compressed groove 21.

Here, the extension line L may be typified by an extension of a line passing through the center (centerline) of the compressed groove or an extension of a line having the width of the groove. The extension line L may be a tangent to the end of the central compressed groove 21 if the central compressed groove 21 is curved in a circular arc. Furthermore, if the central compressed groove 21 extends substantially straight on its end side, it may be an extension of the straight line. Additionally, if the central compressed groove 21 is curved but is almost straight, it may be a line extending parallel to the longitudinal centerline CL.

When the absorbent article 1 is used, the body fluid is discharged to the body fluid discharge portion corresponding region 13 and possibly to its vicinity, and further diffuses forward, rearward, and to both sides. At this point, the presence of the central compressed grooves 21, 21 reduces lateral diffusion from the body fluid discharge portion corresponding region 13. Therefore, the body fluid is more likely to be guided forward and rearward along the central compressed grooves 21, 21.

Here, when the body fluid is discharged in a relatively large volume or suddenly discharged, or when a relatively large force is applied to the absorbent article during walking or exercise, the body fluid may diffuse forward and/or rearward beyond the ends of the central compressed grooves 21, 21. In this case, the body fluid may diffuse to the front lateral side and/or the rear lateral side. Therefore, this diffusion may cause leakage.

In recent years, there has been an increasing demand for slim-type absorbent articles with a thinner absorber, in order for absorbent articles to be less conspicuous and less discomforting or to facilitate movement when attached. According to such slim-type absorbent articles, the twist of an absorbent article due to movement during walking or exercise in particular is likely to cause diffusion of a body fluid to the front lateral side and/or the rear lateral side as described above, and to cause leakage. Therefore, in the case of putting more emphasis on the prevention of body fluid leakage, conventional configurations have no choice but to increase the volume of the absorber.

In contrast, according to this embodiment, the front lateral side compressed groove includes the two unconnected first compressed groove 231 and second compressed groove 232, and the extension line L of the central compressed groove 21 passes between the end 231a of the first compressed groove 231 and the end 232a of the second compressed groove 232. Therefore, the body fluid guided forward and rearward along the central compressed grooves 21, 21 can be drawn inside the front lateral side compressed groove 23, namely, between the first compressed groove 231 and the second compressed groove 232.

The body fluid drawn between the first compressed groove 231 and the second compressed groove 232 continues to diffuse between the first compressed groove 231 and the second compressed groove 232. The first compressed groove 231 and the second compressed groove 232, however, have a circular arc shape and are arranged such that their inner circular arcs face each other, and the extension line L of the central compressed groove 21 does not pass between the other end 231b of the first compressed groove 231 and the other end 232b of the second compressed groove 232. Therefore, the body fluid entering between the first compressed groove 231 and the second compressed groove 232 does not pass between them, and seeps while touching the first compressed groove 231 and the second compressed groove 232. The body fluid, whose way of passing inside the front lateral side compressed groove 23 differs depending on the volume, viscosity, etc., of the body fluid, diffuses in contact with or along at least one of the first compressed groove 231 and the second compressed groove 232. According to the configuration of FIG. 1, the body fluid moves slightly sideward (outward) along the curve of the circular arc of the first compressed groove 231 closer to the centerline CL, and is thereafter held back by the second compressed groove 232 to be directed toward the centerline CL (inward) or to the front lateral side. This allows good control of body fluid diffusion to the front lateral side.

To put it another way, the body fluid that has diffused forward along the central compressed groove 21 can be controlled to meander in direction. This makes it possible to control the diffusion speed of the body fluid, and to prevent leakage on the front lateral side (leakage on the rear lateral side in the case of the rear lateral side compressed groove 24) even when the body fluid is suddenly discharged.

Furthermore, the central compressed groove 21, the first compressed groove 231, and the second compressed groove 232 are not connected to or do not overlap one another. Therefore, despite a relatively concentrated arrangement of the compressed grooves, the absorber body 8 is not hardened, and a comfortable fit can be maintained. Therefore, the absorbent article 1 of an excellent fit, which is less likely to cause discomfort during wearing, can be provided.

Furthermore, the first compressed groove 231 and the second compressed groove 232 are disposed such that their inner circular arcs face each other, namely, such that the compressed grooves surround a predetermined region. Therefore, it is possible to improve the cushioning properties of the absorber body 8. As a result, because the shape of the absorber body 8 is easily restored even when the body 8 twists because of walking or exercise, the regions of the front lateral side compressed groove 23 and the rear lateral side compressed groove 24 are less likely to flatten out. This makes it possible to prevent the degradation of the function of the absorber 4 and to prevent leakage from the front lateral side and the rear lateral side.

By causing the extension line L of the central compressed groove 21 to pass through the midpoint of a line segment connecting the end 231a of the first compressed groove 231 and the end 232a of the second compressed groove 232, it is possible further improve the body fluid drawing effect.

Furthermore, a distance c between the end of the central compressed groove 21 and the line segment connecting the end (the end closer to the central compressed groove 21) 231a of the first compressed groove 231 and the end (the end closer to the central compressed groove 21) 232a of the second compressed groove 232 is preferably 0.5 to 2 times the length of the line segment connecting the end 231a of the first compressed groove 231 and the end 232a of the second compressed groove 232.

According to this embodiment, as illustrated in FIG. 4, a line segment connecting both ends 231a and 231b of the first compressed groove 231 preferably forms an angle α1 of 30° to 60° with the centerline CL. Furthermore, a line segment connecting both ends 232a and 232b of the second compressed groove 232 as well preferably forms an angle α2 of 30° to 60° with the centerline CL.

Each of the angles α1 and α2 is more preferably an angle of 40° to 35°, and still more preferably an angle of 45°, to the centerline CL. The above-described angular range can improve the action of controlling a sideward body fluid flow or diffusion in particular.

Furthermore, as long as the extension line L of the central compressed groove 21 passes between the end 231a of the first compressed groove 231 and the end 232a of the second compressed groove 232, and does not pass between the end 231b of the first compressed groove 231 and the end 232b of the second compressed groove 232, the angles α1 and α2 may be either equal or different. When the angles α1 and α2 are equal, however, it is possible to prevent the absorber from hardening in a region around the compressed grooves while maintaining the action of controlling sideward body fluid diffusion.

Furthermore, the positions of the two circular arcs of the first compressed groove 231 and the second compressed groove 232 are preferably offset from each other in a direction in which the line segment connecting both ends 231a and 231b of the first compressed groove 231 extends or in a direction in which the line segment connecting both ends 232a and 232b of the second compressed groove 232 extends. For example, as illustrated in FIG. 5, in a direction in which a straight line X1 including the line segment connecting both ends 231a and 231b of the first compressed groove 231 extends, the position of the end 231a of the first compressed groove 231 may be offset from the position of the end 231a of the second compressed groove 232, and the position of the other end 231b of the first compressed groove 231 may be offset from the position of the other end 232*b* of the second compressed groove 232.

Specifically, in the direction in which the line segment connecting both ends 231*a* and 231*b* of the first compressed groove 231 extends, the end 232*a* of the second compressed groove 232 closer to the central compressed groove 21 may be offset to one side in the above-described direction relative to the position of the end 231*a* of the first compressed groove 231 closer to the central compressed groove 21, and the end 232*b* of the second compressed groove 232 more distant from the central compressed groove 21 may be offset to the one side relative to the position of the end 231*b* of the first compressed groove 231 more distant from the central compressed groove 21.

The offset arrangement of the first compressed groove 231 and the second compressed groove 232 as described above makes it possible to provide an entrance for a body fluid flowing into the front lateral side compressed groove 23 with an appropriate width and to facilitate directing the body fluid inside the front lateral side compressed groove 23. Therefore, the action of drawing in a body fluid between the first compressed groove 231 and the second compressed groove 232 and the action of guiding a body fluid by causing the body fluid to meander are further improved. Accordingly, even when the body fluid is suddenly discharged, it is possible to satisfactorily prevent leakage from the side in particular. Furthermore, it is also possible to prevent excessive compression and hardening of the absorber due to excessive proximity of the compressed grooves.

Furthermore, as illustrated in FIG. 5, in the direction in which the straight line X1 including the line segment connecting both ends 231*a* and 231*b* of the first compressed groove 231 extends, a distance d between a midpoint O1 of the line segment connecting both ends 231*a* and 231*b* of the first compressed groove 231 and the end 232*a* of the second compressed groove 232 closer to the central compressed groove 21 is preferably 0 to 0.15 times a length D of the line segment connecting both ends 231*a* and 231*b* of the first compressed groove 231. In particular, the midpoint O1 of the line segment connecting both ends 231*a* and 231*b* of the first compressed groove 231 and the end 232*a* of the second compressed groove 232 closer to the central compressed groove 21 are preferably disposed to match in position in the direction in which the straight line X1 extends in the direction in which the straight line X1 extends. Furthermore, the midpoint O1 of the line segment connecting both ends 231*a* and 231*b* of the first compressed groove 231 and the end 232*a* of the second compressed groove 232 are preferably disposed such that the end 232*a* of the second compressed groove 232 is closer to the centerline CL than the midpoint O1 because this makes it possible to more satisfactorily cause the capillary action to occur.

Because the first compressed groove 231 and the second compressed groove 232 are offset a predetermined distance as described above, it is possible to further improve the action of drawing in a body fluid between the first compressed groove 231 and the second compressed groove 232. Furthermore, because it is possible to prevent the absorber from hardening, it is possible to further improve a fit.

The length of the line segment connecting both ends 231*a* and 231*b* of the first compressed groove 231 and/or the length of the line segment connecting both ends 232*a* and 232*b* of the second compressed groove 232 are preferably approximately 10 to 20 mm because this makes it possible to reduce coarseness while maintaining the body fluid drawing action.

According to this embodiment, as illustrated in FIG. 4, a distance e between the line segment connecting both ends 231*a* and 231*b* of the first compressed groove 231 and the line segment connecting both ends 232*a* and 232*b* of the second compressed groove 232 may be 0 to 0.2 times the length of the line segment connecting both ends 231*a* and 231*b* of the first compressed groove 231 closer to the centerline CL. Here, the distance e may be the shortest distance between the line segment connecting both ends 231*a* and 231*b* of the first compressed groove 231 and the line segment connecting both ends 232*a* and 232*b* of the second compressed groove 232.

Preferably, the line segment connecting both ends 231*a* and 231*b* of the first compressed groove 231 and the line segment connecting both ends 232*a* and 232*b* of the second compressed groove 232 are separated. For example, the distance e is preferably approximately 0.05 to 0.15 times the length of the line segment connecting both ends 231*a* and 231*b* of the first compressed groove 231. This configuration makes it possible to further improve the effect of drawing in a body fluid between the first compressed groove 231 and the second compressed groove 232 and to reduce coarseness.

When the distance e is zero, namely, when the line segment connecting both ends 231*a* and 231*b* of the first compressed groove 231 and the line segment connecting both ends 232*a* and 232*b* of the second compressed groove 232 overlap in position in the direction in which the line segment connecting both ends 231*a* and 231*b* of the first compressed groove 231 extends, it is preferable that the end 231*a* of the first compressed groove 231 and the end 232*a* of the second compressed groove 232 be offset from each other and the other end 231*b* of the first compressed groove 231 and the other end 232*b* of the second compressed groove 232 be offset from each other in the direction in which the line segment connecting both ends 231*a* and 231*b* of the first compressed groove 231 extends as described above. This makes it possible to form a region in which a body fluid can satisfactorily diffuse and be retained between the first compressed groove 231 and the second compressed groove 232.

Furthermore, as in the illustrated embodiment, the line segment connecting both ends 231*a* and 231*b* of the first compressed groove 231 and the line segment connecting both ends 232*a* and 232*b* of the second compressed groove 232 preferably extend substantially parallel to each other. Here, being substantially parallel does not indicate being exactly parallel, and allows formation of an angle of ±15° or less, preferably ±5° or less.

The circular arc shape of each of the first compressed groove 231 and the second compressed groove 232 is preferably a circular arc having an angle of 135° to 180°. The above-described angle makes it possible to prevent hardening of the body 8 due to excessive proximity of the compressed grooves while maintaining the action of drawing in a body fluid between the first compressed groove 231 and the second compressed groove 232 facing each other.

While the first compressed groove and the second compressed groove have a circular arc shape, a circle includes not only a true circle but also an ellipse according to this embodiment. Therefore, the arcs of the first compressed grooves and the second compressed grooves of the front lateral side compressed groove 23 and the rear lateral side compressed groove 24 may be either part of a true circle or part of an ellipse, or have a shape including part of a circle or an ellipse, both ends of which can approximate a straight line.

Figure 6:
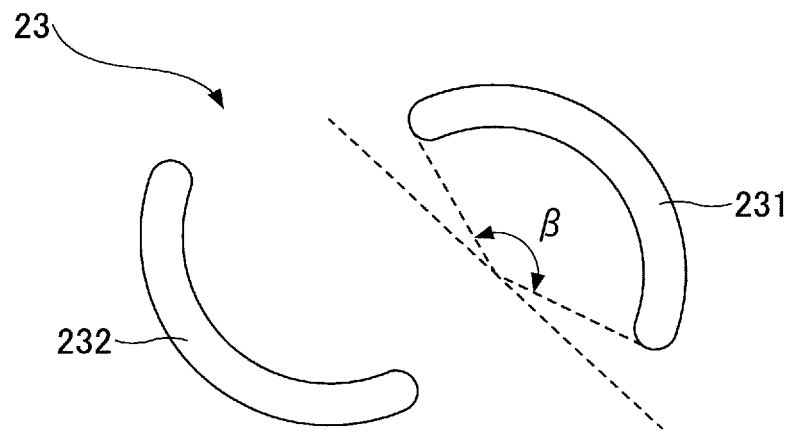
FIG. 6 is a diagram illustrating other shapes of the compressed grooves of the absorbent article according to the embodiment.
Figure 6:
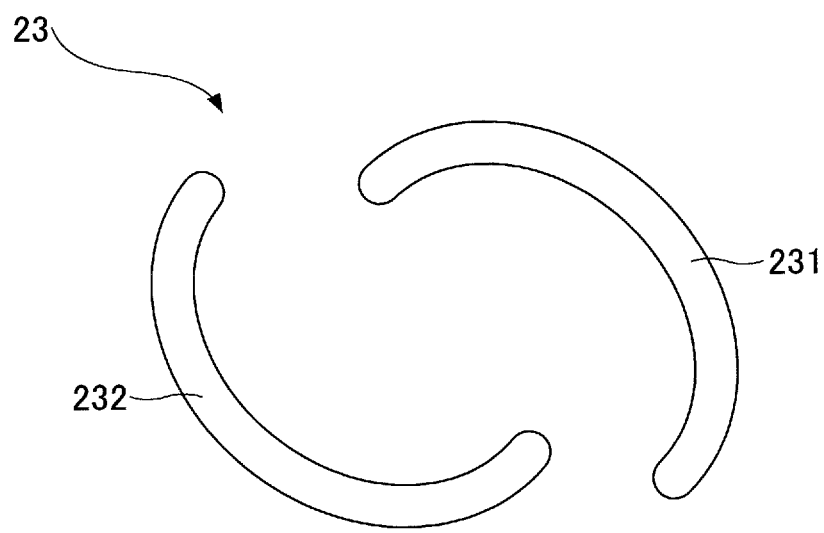

FIG. 6 illustrates other configurations of the first compressed groove 231 and the second compressed groove 232. FIG. 6(a) illustrates the first compressed groove 231 and the second compressed groove 232 whose circular arcs each have an angle β of approximately 150°. Such a shape makes it possible to prevent hardening of the body 8 due to excessive proximity of the compressed grooves. Therefore, it is possible to prevent coarseness and improve a fit for small-sized absorbent articles as well.

FIG. 6(b) illustrates the first compressed groove 231 and the second compressed groove 232 each of which is part of an elliptical shape. This shape makes it possible to increase the diffusion distance of a body fluid, so that it is possible to satisfactorily prevent leakage even when the body fluid is suddenly discharged. Furthermore, because it is possible to prevent hardening of the body 8 due to excessive proximity of the compressed grooves, it is also possible to contribute to reduction in discomfort.

The present application is based on and claims priority to Japanese patent application No. 2016-229539, filed on Nov. 25, 2016, the entire contents of which are hereby incorporated herein by reference.

DESCRIPTION OF THE REFERENCE NUMERALS 1 absorbent article
2 bottom sheet
3 top sheet
4 absorber
5 enveloping sheet
7 side nonwoven fabric
8 body (absorbent article body)
13 body fluid discharge portion corresponding region
21 central compressed groove
23 front lateral side compressed groove
24 rear lateral side compressed groove
25 front compressed groove
26 rear compressed groove
231 first compressed groove of front lateral side compressed groove
231a, 231b end of first compressed groove of front lateral side compressed groove
232 second compressed groove of front lateral side compressed groove
232a, 232b end of second compressed groove of front lateral side compressed groove
241 first compressed groove of rear lateral side compressed groove
242 second compressed groove of rear lateral side compressed groove
CL centerline in front-rear direction
DE dot embossment
E embossment having a shape
L extension line of central compressed groove
WG wing

The invention claimed is:

1. An absorbent article including an elongated body, the body including a liquid-permeable top sheet, a liquid-impermeable bottom sheet, and an absorber provided between the top sheet and the bottom sheet, wherein:
compressed grooves are formed in the body from the top sheet toward the bottom sheet,
the compressed grooves include a pair of central compressed grooves formed substantially along a longitudinal direction of the body in line symmetry with respect to a centerline extending in the longitudinal direction of the body serving as an axis of symmetry, a pair of front lateral side compressed grooves formed in line symmetry with respect to the centerline serving as an axis of symmetry on a front lateral side of the central compressed grooves, and a pair of rear lateral side compressed grooves formed in line symmetry with respect to the centerline serving as an axis of symmetry on a rear lateral side of the central compressed grooves,
each of the pair of the front lateral side compressed grooves and the pair of the rear lateral side compressed grooves includes a first compressed groove and a second compressed groove positioned more distant from the centerline than the first compressed groove,
the first compressed groove and the second compressed groove have a circular arc shape, and are disposed such that inner circular arcs of both compressed grooves face each other, and
an extension line of the central compressed grooves passes between an end of the first compressed groove and an end of the second compressed groove, and does not pass between another end of the first compressed groove and another end of the second compressed groove.

2. The absorbent article as claimed in claim 1, wherein a line segment connecting both ends of the first compressed groove and a line segment connecting both ends of the second compressed groove form an angle of 30° to 60° with the centerline.

3. The absorbent article as claimed in claim 1, wherein
in a direction in which a line segment connecting both ends of the first compressed groove extends,
the end of the second compressed groove closer to the central compressed grooves is offset to one side in the direction relative to the end of the first compressed groove closer to the central compressed grooves, and
the end of the second compressed groove more distant from the central compressed grooves is offset to the one side in the direction relative to the end of the first compressed groove more distant from the central compressed grooves.

4. The absorbent article as claimed in claim 3, wherein
in the direction in which the line segment connecting both ends of the first compressed groove extends,
a distance between a midpoint of the line segment connecting both ends of the first compressed groove and the end of the second compressed groove closer to the central compressed grooves is 0 to 0.15 times a length of the line segment connecting both ends of the first compressed groove.

5. The absorbent article as claimed in claim 3, wherein a distance between the line segment connecting both ends of the first compressed groove and the line segment connecting both ends of the second compressed groove is 0 to 0.2 times a length of the line segment connecting both ends of the first compressed groove.

6. The absorbent article as claimed in claim 1, wherein the first compressed groove and the second compressed groove has a shape of a circular arc having an angle of 135° to 180°.

* * * * *